(12) United States Patent
Bolz

(10) Patent No.: US 7,057,424 B2
(45) Date of Patent: Jun. 6, 2006

(54) DIAGNOSE INTERFACE FOR A NON-ISOLATED SENSOR

(75) Inventor: Stephan Bolz, Pfatter (DE)

(73) Assignee: Siemens Aktiengesellschaft, Munich (DE)

(*) Notice: Subject to any disclaimer, the term of this patent is extended or adjusted under 35 U.S.C. 154(b) by 419 days.

(21) Appl. No.: 10/306,116

(22) Filed: Nov. 27, 2002

(65) Prior Publication Data

US 2004/0099530 A1    May 27, 2004

(51) Int. Cl.
*H03K 3/00* (2006.01)
(52) U.S. Cl. ...................................... 327/108; 327/308
(58) Field of Classification Search ........ 327/108–112, 327/308, 312, 318, 319
See application file for complete search history.

(56) References Cited

U.S. PATENT DOCUMENTS 5,187,674 A * 2/1993 Bonne .......................... 702/50

OTHER PUBLICATIONS

National Semiconductor; LM9040 Dual Lambda Sensor Interface Amplifier; Aug. 1995.

* cited by examiner

*Primary Examiner*—Kenneth B. Wells
(74) *Attorney, Agent, or Firm*—Baker Botts L.L.P.

(57) ABSTRACT

A circuit arrangement for coupling with a sensor having two output terminals is disclosed wherein one terminal is coupled to a first ground and the circuit arrangement is coupled with a second ground. The circuit arrangement comprises an attenuator coupled with the output terminals of the sensor, first and second buffers coupled with the attenuator to generate respective output signals, a differential amplifier receiving the output signals of the buffers, and a current source generating a bias current which is fed to the input terminal not coupled with ground.

20 Claims, 4 Drawing Sheets

DIAGNOSE INTERFACE FOR A NON-ISOLATED SENSOR

BACKGROUND OF THE INVENTION

The present invention relates generally to a circuit arrangement used as an interface for a sensor, in particular, for a pumped reference oxygen sensor used in combination with a combustion engine.

Oxygen sensors are particularly used in combination with combustion engines using controlled catalytic converters. The use of catalytic converters in cars started much earlier in the USA in comparison with Europe. However, innovation cycles are often slower in the US automotive technology. Therefore, often older technology is used for longer periods in the USA as compared to European countries. For example, the binary lambda oxygen sensor which is used to regulate the gasoline mixture in a combustion engine, comprises the negative terminal being electrically coupled with the sensor housing in embodiments of the first generation. The reasons for this connection relates to an easier and cheaper construction. However, this construction also results in an electrical coupling between the sensor housing and the engine through the fixture of the sensor within the muffler arrangement. This connection is disadvantageous because shifted ground potentials within a motor vehicle. For example, the engine ground is usually more negative than the ground of the motor control unit. This potential shift is due to switching of high load currents, e. g., 10 . . . 15A, and the inner resistance of the ground wires, e. g. 20 . . . 40 mΩ. Typical voltage shifts are in the range of −300 . . . +600 mV. In addition, any on/off switching of high loads causes voltage overlay peaks of up to multiple 100 m $V_{ss}$. These ground distortions and overlay voltages can cause serious problems with respect to evaluation of the respective sensor signals and may render the actual sensor signals completely useless.

Oxygen sensors according to newer technology are, therefore, fully isolated and, thus, avoid any electrical coupling with the engine. However, oxygen sensors of the first generation are still widely used, in particular, in the United States because of their lower manufacturing costs. Therefore, modern motor control units must be able to interface with these kind of sensors which are not fully isolated. To this end, specific interface circuits used to be available which allowed for the evaluation of sensors whose housing is electrically coupled with the engine and thus with the motor vehicle ground.

FIG. 4 shows an example of such a known circuit. A sensor 400 which is connected with the engine ground is coupled through resistors 430 and 415 with the input terminals of the interface circuit proper. Capacitors 425 and 435 are coupled between the input terminals of the interface circuit and the interface ground. One of the sensor connections is furthermore coupled through resistor 410 with a supply voltage Vcc and through capacitor 420 with the interface ground. The interface circuit comprises a first switch 440 which is coupled with the input terminals. The switch output is coupled through a capacitor 445 with the input of a second switch 460 and through capacitor 450 with the input of a third switch 455. The first output of switch 455 is connected with the supply voltage Vcc. The second output of switch 455 and the first output of switch 460 are coupled with the interface ground. The second output of switch 460 is connected to the inverting input of an integrator consisting of operational amplifier 475 and capacitor 470 in its feedback loop. A fourth switch couples the inverting input of the integrator with either the supply voltage or the output of the integrator. The output of the integrator is coupled with the first input of a fifth switch 495 which is controlled by the output signal of a comparator 405. The second input of switch 495 is coupled through resistor 490 with the supply voltage. The first input of comparator 405 is coupled with the second interface input terminal and the second input of comparator 405 receives a voltage signal being equal to half the supply voltage. Furthermore, a timing circuit is provided which generates control signals for switches 440, 455, 460, and 480.

All switches are implemented as CMOS switches. Capacitor 445 is used as a transfer capacitor for eliminating the common mode of the input signal. To this end, the capacitor is switched in a first position between interface ground and the second input terminal and in a second position between the inverting input of operational amplifier 475 and the first interface input terminal with a high frequency. Thus, the CMOS switch operates like a resistor. Capacitor 465 operates as a feedback capacitor in a similar way. These two capacitors operating as resistors form together with the operational amplifier/integrator an inverting amplifier. The bias capacitor 450 together with CMOS switch 455 are used to generate a small bias current which is fed to the sensor 400 and which will not influence the measurement when the sensor is in operating mode, i.e. the sensor has low resistance.

One of the disadvantages of this circuit arrangement is that the CMOS switches at the input of the circuit must comply with a high standard. This renders this circuit expensive and interference-prone. In addition, this circuit must withstand the required negative input voltages. thus, additional protective measurements, such as, isolation and charge pumps (not shown) must be provided. Furthermore, the CMOS switches must be able to tolerate a relatively high input voltage of up to 12V in case of a short circuit of the sensor. This is particularly difficult because the supply voltage is usually only 5V. Integrated circuits using this technology need furthermore additional isolation/separation measurements if more than one interface circuit is provided to prevent any cross over influence of the channels and to prevent a latch-up.

The bias current generated by switch 455 and capacitor 450 is used to detect a connection failure between the first input terminal and the sensor. In such a case, the bias current will overdrive the operational amplifier. A similar scenario takes place in case of a short circuit between the first input terminal and the positive terminal of the battery. The output voltage in both cases will be approximately 0V. To detect any interruption between the second input terminal and the sensor additional circuitry is necessary. This additional circuitry is shown in FIG. 4 with resistor 410, capacitor 420, comparator 405 and CMOS switch 495. During normal operation the current generated by resistor 410 will flow to the engine ground through the electrical coupling of the housing of sensor 400 and will not influence the measurement. However, in case of an interruption of this connection the potential at the second input terminal will raise to the supply voltage, for example, 5V. In case of a normal operational temperature of the sensor, i.e. low resistance of the sensor, the operational amplifier will be driven to its positive limit, e.g., 5V. However, in case of a cold sensor (during the start up phase of the engine) the sensor will have a high resistance and the internally generated bias current will put the circuit into an undefined state. To prevent such a state, comparator 405 will compare the potential at the second input terminal with Vcc/2. If the potential is above this threshold, comparator 405 will control switch 490 to select a constant output voltage to signalize this error.

As described above, the prior art interface circuit is highly cumbersome and requires additional evaluation of the generated output signal. Furthermore, this type of interface circuit is not in production anymore and, thus, not available for new construction which specifies the use of a non-isolated sensor.

SUMMARY OF THE INVENTION

It is therefore an object of the present invention to provide an interface circuit for any type of non-isolated sensor which overcomes the above mentioned problems.

This object is achieved by an embodiment according to the present invention which provides a circuit arrangement for coupling with a sensor having two output terminals wherein one terminal is coupled to a first ground and the circuit arrangement is coupled with a second ground. The circuit arrangement comprises an attenuator coupled with the output terminals of the sensor, first and second buffers coupled with the attenuator to generate respective output signals, a differential amplifier receiving the output signals of the buffers, and a current source generating a bias current which is fed to the input terminal not coupled with ground.

Another embodiment of the present invention is an engine control unit for a motor vehicle comprising an oxygen sensor within a catalytic converter unit having two output terminals wherein one terminal is coupled to the engine ground, an interface circuit arrangement for coupling with the sensor wherein the interface circuit arrangement is coupled with an interface ground and at least one supply voltage, an attenuator coupled with the output terminals of the sensor, first and second buffers coupled with the attenuator to generate respective output signals, a differential amplifier receiving the output signals of the buffers, and a current source generating a bias current which is fed to the non-grounded input terminal.

The attenuator can be a resistor network and the buffers can be operational amplifiers. The attenuator may reduce the input signal by a first factor, whereby the differential amplifier may comprise an amplification factor equal to the first factor. The current source can comprise a current mirror. The resistor network can comprise first, second, and third resistors coupled in series between the first and second output terminal of the sensor, wherein the attenuator output is formed by the middle resistor of the three resistors connected in series. The operational amplifiers can receive the input signal at their non-inverting input and the output signal may be fed back to their inverting input, respectively. The input of the operational amplifiers can be coupled with the interface ground through a respective capacitor. The operational amplifiers may receive a first and second supply voltage of +5V and −1V, respectively. The sensor can be an oxygen sensor for use in a catalytic converter.

A method of operating an interface circuit for a non-isolated sensor in a motor vehicle, can comprise the steps of:
receiving a first and second signal from the sensor, wherein the second signal is an engine ground signal;
attenuating the first and second signal;
buffering the first and second signal;
generating a differential signal from the two buffered signals;
generating a bias current and feeding the bias current the sensor.

The method may further comprise the steps of digitally converting the differential signal, and analyzing the digital signal. An error signal can be generated in case the digital signal represents a constant value for a predetermined time and/or in case the digital signal represents a constant value after predetermined time. The error signal can in furthermore be generated in case the digital signal represents a constant value of approximately 0V and/or in case the digital signal represents a constant value which is greater than a predetermined threshold value.

BRIEF DESCRIPTION OF THE DRAWINGS

A more complete understanding of the present disclosure and advantages thereof may be acquired by referring to the following description taken in conjunction with the accompanying drawings, in which like reference numbers indicate like features, and wherein.

DETAILED DESCRIPTION OF THE PREFERRED EMBODIMENTS

Figure 1:
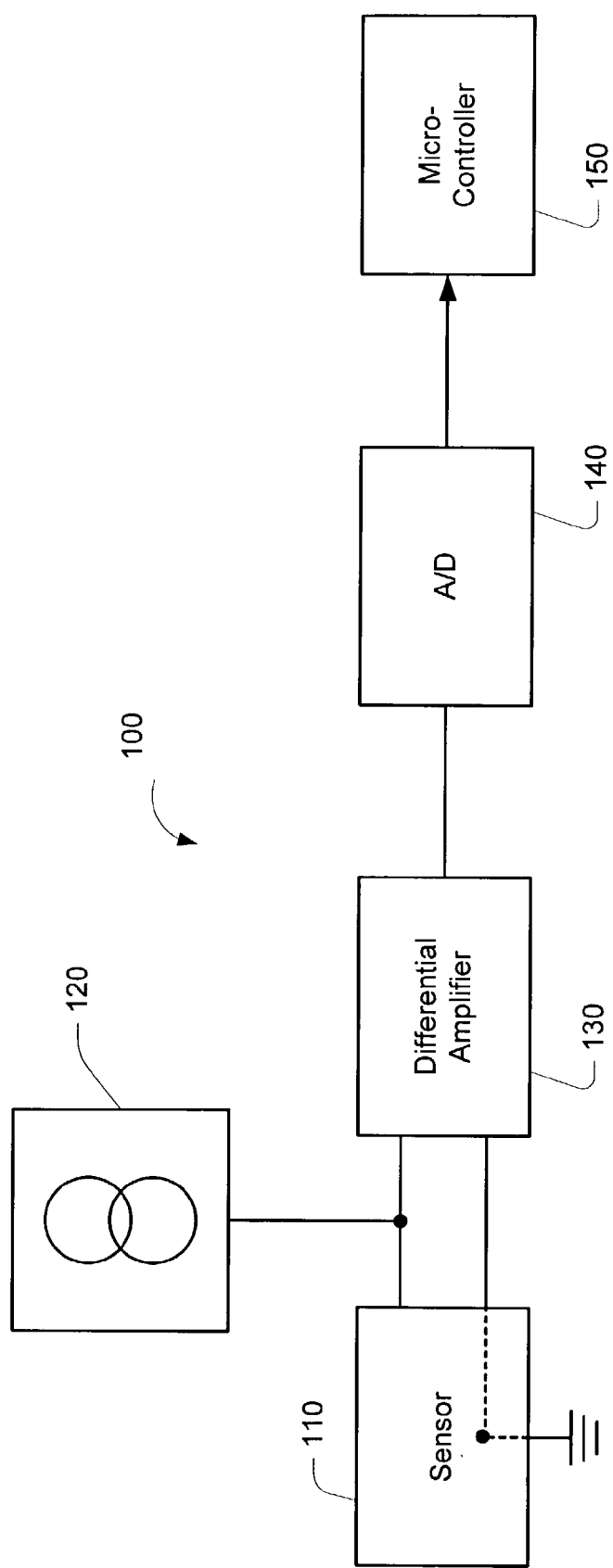
FIG. 1 shows a block diagram of the interface circuit according to the present invention.

FIG. 1 shows a block diagram depicting the overall evaluation circuit for a non-isolated sensor having its housing or one output terminal coupled with ground. The sensor 110 comprises two output lines wherein one is connected to ground, e.g. through the housing of the sensor. The interface circuit consists of a current source for biasing the output line of the sensor not connected to ground and a special differential amplifier unit 130. This differential amplifier unit 130 generates an output signal which is fed to an analog-to-digital converter 140 which converts the analog signal into a digital representation which again is then fed to microcontroller 150.

The differential amplifier 130 comprises two stages as will be explained in more detail below. The first stage comprises separate operational amplifiers for each output line of the sensor 110. The output signals of these two operational amplifiers are then fed to a differential amplifier which generates the output signal proper. The overall amplification is chosen to be 1, thus, the sensor output signal is not altered with respect to its content.

Figure 2:
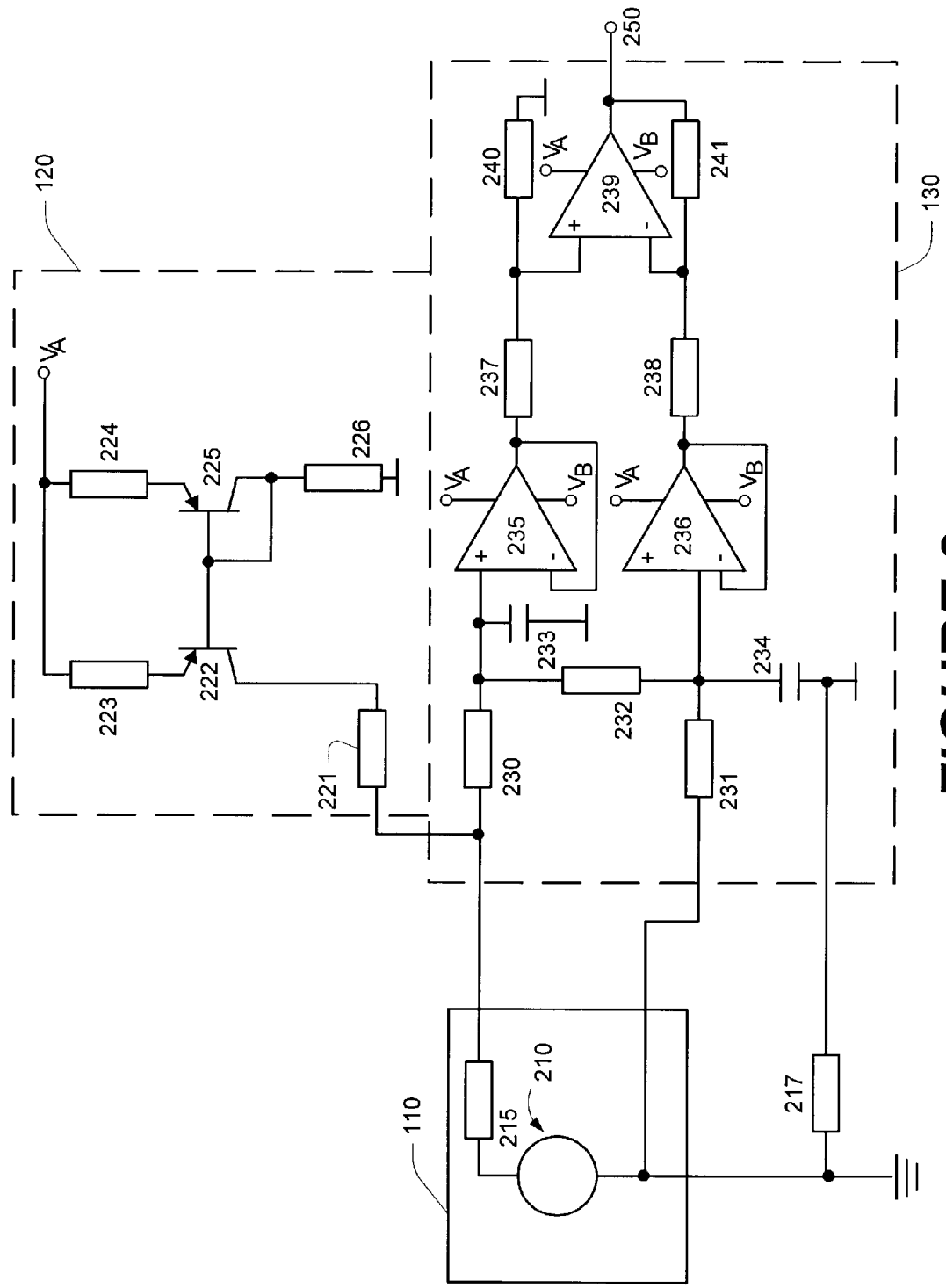
FIG. 2 shows a more detailed embodiment of the circuit depicted in FIG. 1.

FIG. 2 shows a more detailed circuit diagram of the interface circuit coupled with the non-isolated sensor. Sensor 110 is depicted as a substitute circuit including a voltage source 210 and a resistor 215 connected in series for generating the sensor output signal. The second output terminal of the two output terminals is coupled with the engine ground due to the construction of a non-isolated sensor. The first output terminal is connected through a resistor 230 with the non-inverting input of a first operational amplifier 235 and through resistor 221 with the collector of a first transistor 222. The emitter of transistor 222 is receiving a first supply voltage $V_A$ through resistor 223. The base of transistor 222 is coupled with the base and the collector of a second transistor 225 as well as with the interface ground through resistor 226. As mentioned above engine ground and interface ground are due to the construction of a motor vehicle usually not on the same potential. In this circuit engine ground and circuit ground are coupled through a resistor 217. The emitter of transistor 225 is also receiving the first supply voltage $V_A$ through resistor 224. The second output of sensor 110 is coupled through resistor 231 with the non-inverting input of a second operational amplifier 236. Both non-inverting inputs of operational amplifiers 235 and 236 are connected through resistor 232 and each input is coupled through a capacitor 233 and 234, respectively with the interface ground. Each output of the operational amplifiers 235 and 236 are connected with the respective inverting input and through a resistor 237 and 238, respectively with the first and second input of a differential amplifier 239. The first and non-inverting input of differential amplifier 239 is further coupled through resistor 240 with the interface ground whereas the inverting input of differential amplifier 239 is coupled through resistor 241 with its output. The output of differential amplifier is connected to output terminal 250. Each operational and differential amplifier 235, 236, and 239 receive the first supply voltage $V_A$ and a second supply voltage $V_B$.

Resistors 230, 231, and 232 form an attenuator or input network that reduces the input signal by a factor, of e.g., ⅓. This attenuator or network thereby performs a protection function for the following circuit. In addition, capacitors 233 and 234 in combination with this network constitute an efficient protection against electromagnetic interferences. The operational amplifiers 235 and 236 operate as buffers. These buffers operate with the supply voltages $V_A$ and $V_B$ which, for example, in a automotive control unit includes a supply voltage of +5V and −1V. These buffers are so-called rail-to-rail amplifiers. The resistors 237, 238, and 241 are chosen such that the differential amplifiers has an amplification factor of 3 whereby the input dampening factor of ⅓ is compensated. The overall amplification is, thus, equal to 1. Transistors 222 and 225 in combination with resistors 223, 224, and 221 form a current mirror which feeds a constant current to the first output terminal of the sensor 110. For example, this current mirror can have a ratio of 10:1 by a respective design of resistors 223 and 224 and a current of 5 μA through resistor 226 translates into an output current of 0.5 μA=500 nA.

The resistor network 230, 231, and 232 and the bias current mirror has the following effect: The input of the following operational amplifiers are protected from electromagnetic interferences and overvoltage. Furthermore, the current mirror allows for diagnose of any error. During normal operation there are two different phases. The first phase takes place during the warming up period when the sensor is still cold and, thus, has a high resistance. The constant bias current which is introduced through resistor 221 will mainly flow through resistors 230, 232, and 231 towards engine ground. The voltage which is thereby generated across resistor 232 will be in the range of 450 mV. This value will be converted by the analog-to-digital converter 140 and the software running in microcontroller 150 will interpret this as normal operation. Any common mode due to shifts between engine ground and interface ground will be eliminated by the differential amplifier. The second phase takes place when the sensor reaches its normal operating temperature. Now the constant bias current will more and more flow through the sensor and the input voltage will be more defined by the voltage source 210. The analog-to-digital converter will now receive a signal with rising amplitude whose mean value will be near 450 mV. Once the sensor reached its final operating temperature, the constant current will have no effect and the voltage source 210 will determine the input voltage. The analog-to-digital converter 140 will now receive the sensor signal which usually will be between 200 mV . . . 800 mV.

During a failure of the sensor, the arrangement as shown in FIG. 2 will have the following effect. For example, in case of a coupling failure when the first output terminal gets disconnected from the interface input, the resistor network 230, 231, 232 will constantly receive the bias current and the output will constantly generate a voltage of approximately 450 mV. The software will now recognize this constant voltage and after a predetermined time exceeding the warming up phase, during which this output voltage is valid, will generate an error signal. In addition the system can monitor the warm-up current in the warm-up circuit. However, whenever the output voltage remains on a constant value, the system software will determine such a state as an error or time out.

In case of an interruption or breaking of the connection between the second output terminal of the sensor and the interface circuit, the constant current cannot flow towards the engine ground anymore. Thus, both inputs of the interface circuit will have the same potential which is defined by the sensor voltage. However, the differential voltage will be 0 and, thus, the monitor software will recognize this as an error. In case of a short circuit of the first output terminal with ground, a similar output voltage, namely 0V will be generated which again will be recognizable by the monitor software. In case of a short circuit towards the positive battery terminal or supply voltage, the differential voltage at the input of the interface will be constantly greater that 5V which again can be easily detected by the monitor software. In case of a short circuit of the second terminal with the positive battery terminal will generally cause a major short circuit because the second sensor output terminal is directly coupled with battery ground and, thus, cause a respective fuse or the wire to melt. In the first scenario the car will require service whereas in the second scenario one of the above explained scenarios will take place. In any case, the interface circuit will not be damaged.

Figure 3:
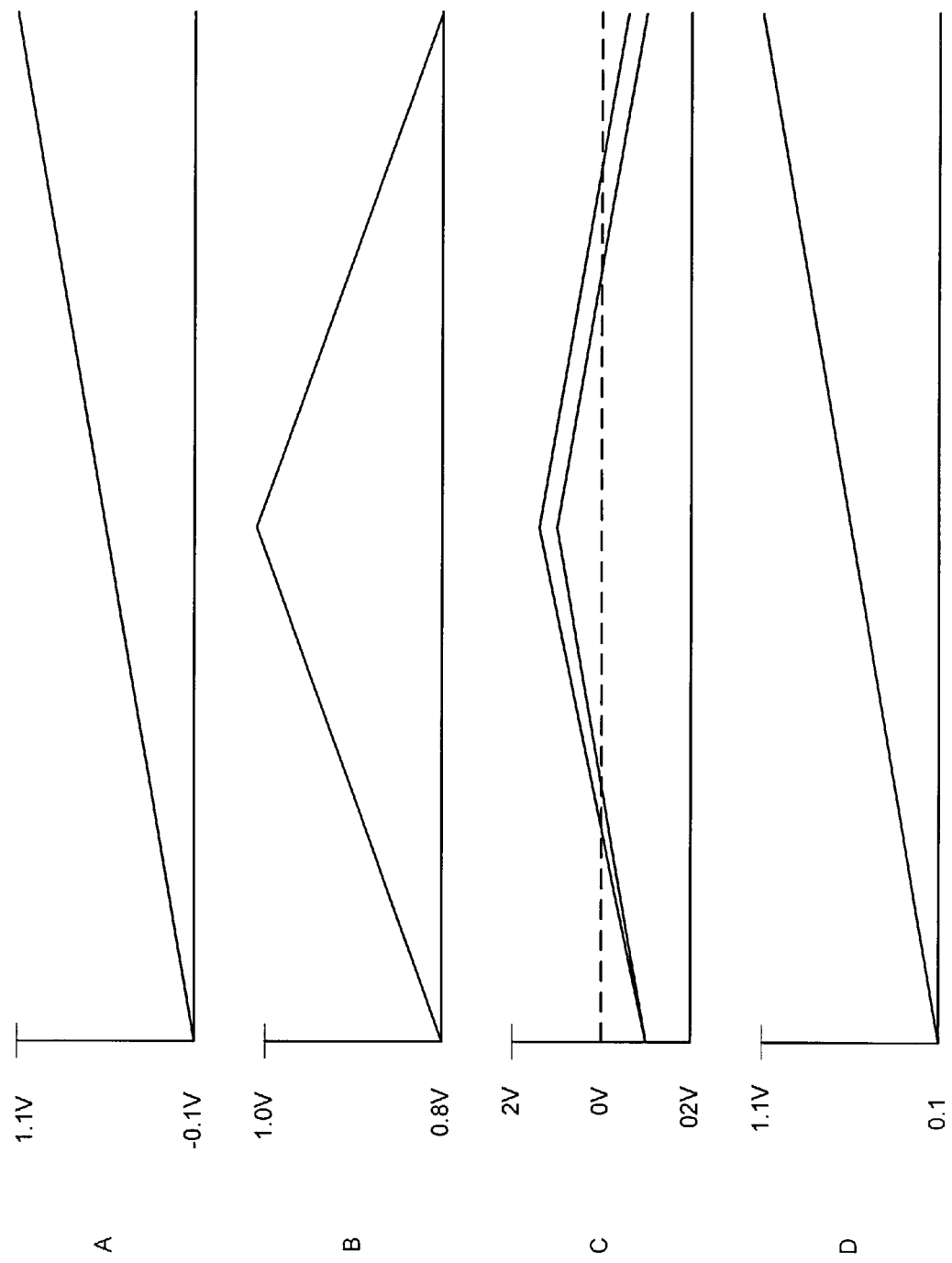
FIG. 3 shows certain signals of the circuit as depicted in FIG. 2.
Figure 4:
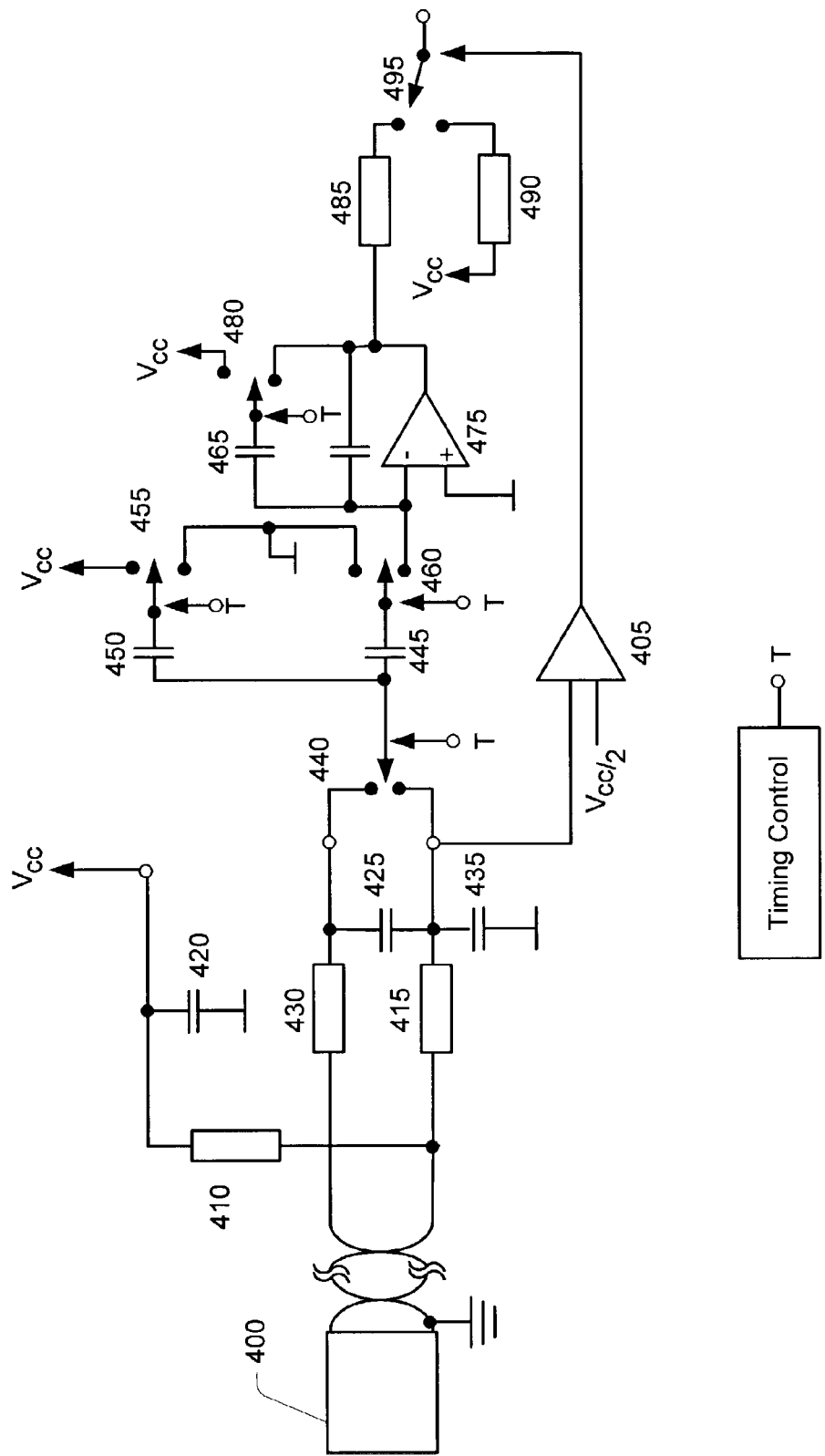
FIG. 4 shows an interface circuit according to the prior art.

FIG. 3 shows in FIG. 3A the sensor output signal which can vary between −0.1V and 1.1V. FIG. 3B shows exemplary the full range of common mode error signal which can typically vary from −0.8V to 1.0V. These signals combined may, thus, form the input signal and are represented in FIG. 3C for the non-inverting input of operational amplifier 235 and 236, respectively. Finally, FIG. 3D shows the output signal generated by the interface circuit according to the present invention which shows the sensor signal without any interference from the signal shown in FIG. 3B.

The present invention is suitable for any kind of sensor which is non-isolated, i.e. one terminal is permanently coupled with the housing and, thus, with ground. The overall amplification is not necessarily limited to 1 but can also be greater or less than 1 depending on the following evaluation circuit. Furthermore the attenuator or input network can reduce the input signal by any appropriate factor dependent on the value of the possible interference signal.

What is claimed is:

1. A circuit arrangement for coupling with a sensor having first and second output terminal wherein the first output terminal is connected to a first ground potential and the circuit arrangement is coupled with a second ground potential wherein the first ground potential is coupled with the second ground potential, the circuit arrangement comprising:
    an attenuator coupled with the first and second output terminals of the sensor;
    first and second buffers coupled with the attenuator to generate respective output signals;

a differential amplifier receiving the output signals of the buffers; and a current source generating a bias current which is fed to the second output terminal.

2. A circuit arrangement according to claim 1, wherein the attenuator is a resistor network.

3. A circuit arrangement according to claim 1, wherein the buffers are operational amplifiers.

4. A circuit arrangement according to claim 1, wherein the attenuator reduces the input signal by a first factor and whereby the differential amplifier comprises an amplification factor equal to the first factor.

5. A circuit arrangement according to claim 1, wherein the current source comprises a current mirror.

6. A circuit arrangement according to claim 2, wherein the resistor network comprises first, second, and third resistors coupled in series between the first and second output terminal of the sensor, wherein the attenuator output is formed by the middle resistor of the three resistors connected in series.

7. A circuit arrangement as in claim 3, wherein the operational amplifiers receive an input signal at their non-inverting input and generate an output signal which is fed back to their inverting input, respectively.

8. A circuit arrangement according to claim 3, wherein the input of the operational amplifiers are coupled with the second ground potential through a respective capacitor.

9. A circuit arrangement according to claim 1, wherein the operational amplifiers receive a first and second supply voltage of +5V and 1V, respectively.

10. A circuit arrangement according to claim 1, wherein the sensor is an oxygen sensor for use in a catalytic converter.

11. A method of operating an interface circuit for a non-isolated sensor having first and second terminals in a motor vehicle, wherein the second output terminal is connected to a first ground potential and the circuit arrangement is coupled with a second ground potential wherein the first ground potential is coupled with the second ground potential, comprising the steps of:

receiving a first and second signal from the first and second terminals of the sensor, wherein the second signal is an engine ground signal;

attenuating the first and second signal;

buffering the first and second signal;

generating a differential signal from the two buffered signals; and generating a bias current and feeding the bias current to the first terminal of the sensor.

12. A method according to claim 11, further comprising the steps of:

digitally converting the differential signal; and analyzing the digital signal.

13. A method according to claim 12, wherein an error signal is generated in case the digital signal represents a constant value for a predetermined time.

14. A method according to claim 12, wherein an error signal is generated in case the digital signal represents a constant value after a predetermined time.

15. A method according to claim 12, wherein an error signal is generated in case the digital signal represents a constant value of approximately 0V.

16. A method according to claim 12, wherein an error signal is generated in case the digital signal represents a constant value which is greater than a predetermined threshold value.

17. An engine control unit for a motor vehicle comprising:

an oxygen sensor within a catalytic converter unit having first and second output terminals wherein the first terminal is coupled to the engine ground;

an interface circuit arrangement for coupling with the sensor wherein the interface circuit arrangement is coupled with an interface ground and at least one supply voltage;

an attenuator coupled with the first and second output terminals of the sensor;

first and second buffers coupled with the attenuator to generate respective output signals;

a differential amplifier receiving the output signals of the buffers; and a current source generating a bias current which is fed to the second output terminal of the sensor.

18. An engine control unit according to claim 17, wherein the attenuator is a resistor network and the buffers are operational amplifiers.

19. An engine control unit according to claim 17, wherein the attenuator reduces an input signal by a first factor and whereby the differential amplifier comprises an amplification factor equal to the first factor.

20. An engine control unit according to claim 18, wherein the operational amplifiers receive a first and second supply voltage of +5V and −1V, respectively.

* * * * *